(12) United States Patent
Shaw et al.

(10) Patent No.: US 12,106,251 B2
(45) Date of Patent: Oct. 1, 2024

(54) SYSTEMS, METHODS, AND APPARATUS FOR MAPPING PET PRODUCT PERFORMANCE

(71) Applicant: Mars, Incorporated, McLean, VA (US)

(72) Inventors: Jared Shaw, Thompson's Station, TN (US); Lucy Jane Holcombe, Leicestershire (GB); Corryn Wallis, Leicestershire (GB)

(73) Assignee: Mars, Incorporated, McLean, VA (US)

( * ) Notice: Subject to any disclaimer, the term of this patent is extended or adjusted under 35 U.S.C. 154(b) by 257 days.

(21) Appl. No.: 17/011,837

(22) Filed: Sep. 3, 2020

(65) Prior Publication Data

US 2021/0073709 A1 Mar. 11, 2021

Related U.S. Application Data

(60) Provisional application No. 62/897,144, filed on Sep. 6, 2019.

(51) Int. Cl.
*G06Q 10/0639* (2023.01)
*A61D 5/00* (2006.01)
(Continued)

(52) U.S. Cl.
CPC ......... *G06Q 10/06395* (2013.01); *A61D 5/00* (2013.01); *G06T 11/001* (2013.01);
(Continued)

(58) Field of Classification Search
CPC ......... G06Q 10/06395; G06Q 30/0201; A61D 5/00; G06T 11/001; G06T 11/206; G06T 2210/41; G16H 10/20; G16H 15/00; G16H 30/20; G16H 30/40; G16H 50/20; G16H 50/50; G16H 50/70; G16H 40/20;
(Continued)

(56) References Cited

U.S. PATENT DOCUMENTS

| | | | | |
|---|---|---|---|---|
| 6,093,019 A | * | 7/2000 | Morandi | A61C 19/00 433/29 |
| 2002/0021786 A1 | * | 2/2002 | Hamamoto | H04N 25/76 378/189 |

(Continued)

OTHER PUBLICATIONS

D. Herbert, Robert, et al. "Soft Material-Enabled, Flexible Hybrid Electronics for Medicine, Healthcare, and Human-Machine Interfaces." Materials 11.2 (2018): 187 (Year: 2018).*

*Primary Examiner* — Amber A Misiaszek
(74) *Attorney, Agent, or Firm* — Bookoff McAndrews, PLLC

(57) ABSTRACT

The present disclosure relates to a system, apparatus, or method for testing of pet products and their resulting impact on pets. Certain embodiments include collecting, at a server, data related to one or more teeth of a pet, where the data results from the testing of the pet product. Certain embodiments also include mapping, by the server, the data to a heatmap representation of the one or more teeth of the pet. The heatmap representation illustrates a statistical analysis of the data. In addition, certain embodiments determine based on the statistical analysis of the data illustrated in the heatmap representation an impact of the pet product on the one or more teeth of the pet.

16 Claims, 9 Drawing Sheets

(51) Int. Cl.
*G06F 3/0482* (2013.01)
*G06Q 30/0201* (2023.01)
*G06T 11/00* (2006.01)
*G06T 11/20* (2006.01)
*G16H 10/20* (2018.01)
*G16H 15/00* (2018.01)
*G16H 30/20* (2018.01)
*G16H 30/40* (2018.01)
*G16H 50/20* (2018.01)
*G16H 50/50* (2018.01)
*G16H 50/70* (2018.01)

(52) U.S. Cl.
CPC ........... *G06T 11/206* (2013.01); *G16H 10/20* (2018.01); *G16H 15/00* (2018.01); *G16H 30/20* (2018.01); *G16H 30/40* (2018.01); *G16H 50/20* (2018.01); *G16H 50/50* (2018.01); *G16H 50/70* (2018.01); *A61B 2503/40* (2013.01); *G06F 3/0482* (2013.01); *G06Q 30/0201* (2013.01); *G06T 2210/41* (2013.01)

(58) Field of Classification Search
CPC ... G16H 50/30; A61B 2503/40; G06F 3/0482; G06F 3/04847
See application file for complete search history.

(56) References Cited

U.S. PATENT DOCUMENTS

| | | | |
|---|---|---|---|
| 2014/0314819 A1* | 10/2014 | Scherl | A61K 6/20 424/401 |
| 2016/0220196 A1* | 8/2016 | Stapleton | A61B 5/1111 |
| 2016/0367188 A1* | 12/2016 | Malik | G16H 40/67 |
| 2018/0360567 A1* | 12/2018 | Xue | G06F 18/21 |
| 2019/0105842 A1* | 4/2019 | Dau | B33Y 50/00 |
| 2019/0142275 A1* | 5/2019 | Harris | A61B 5/0071 433/1 |
| 2019/0200746 A1* | 7/2019 | Serval | A61B 5/0077 |

* cited by examiner

FIG. 4

SYSTEMS, METHODS, AND APPARATUS FOR MAPPING PET PRODUCT PERFORMANCE

CROSS-REFERENCE TO RELATED APPLICATIONS

This application claims the benefit, under 35 USC Section 119(e) of the U.S. Provisional Application No. 62/897,144, filed Sep. 6, 2019, the disclosure of which is hereby incorporated herein by reference.

1. FIELD OF THE INVENTION

The present disclosure relates to pet products, more particularly to the testing of pet products and their resulting impact on pets.

2. BACKGROUND

The growing emphasis on pet safety and health has resulted in the increased experimentation and testing of pet products. Methodical studies are planned and executed for pet products, by manufacturer, designers, or any other interested party attempting to gage the various effects of pet products on a given pet. The increasing breadth and number of pet product studies has resulted in a growing volume of data related to pet product. Given the sheer volume of data being collected, it has become more difficult to properly analyze the results of pet product studies, increasing the risk of misinterpretation of the data. Misinterpreting data results of pet product studies can potentially be harmful to the safety or health of pets.

Accordingly, there is an ongoing demand in the pet product industry for an apparatus, system, and/or method that allows researchers to better understand the results of pet product studies. In particular, there remains a need for techniques that allow researchers of pet products to collect, analyze, and/or visualize results of studies, while preventing the potential misinterpretation of the resulting data.

3. SUMMARY OF THE INVENTION

The present disclosure relates to a system, apparatus, or method for testing of pet products and their resulting impact on pets. Certain non-limiting embodiments can include a method for pet product testing. Certain non-limiting embodiments of the method can include collecting, at a server, data related to one or more teeth of a pet, where the data results from the testing of the pet product. The method can also include mapping, by the server, the data to a heatmap representation of the one or more teeth of the pet. The heatmap representation can illustrate a statistical analysis of the data. In addition, the method can include determining based on the statistical analysis of the data illustrated in the heatmap representation an impact of the pet product on the one or more teeth of the pet. The data, for example, includes at least one of percentage of plaque or calculus on the one or more teeth or prevalence of periodontal disease for the one or more teeth.

In certain non-limiting embodiments, the method further includes collecting, at the server, additional data related to the one or more teeth of the pet, where the data results from the testing of the another pet product. The method can also further include mapping, by the server, the additional data to another heatmap representation of the one or more teeth of the pet. The another heatmap representation can illustrate a statistical analysis of the data. In addition, the method can include comparing the heatmap representation of the one or more teeth of the pet related to the pet product and the another heatmap representation of the one or more teeth of the pet related to the another pet product. The method can further include choosing the pet product or the another pet product based on the comparing of the heatmap representation and the another heatmap representation.

In certain non-limiting embodiments, the method can include displaying the heatmap representation on a user interface of a terminal device. The determining of the impact of the pet product on the one or more teeth of the pet is based on the displayed heatmap representation. In certain non-limiting embodiments, the method can provide a user with one or more display options for the heatmap representation at the user interface of the terminal device, and changing, at the server, the heatmap representation based on the one or more display options selected by the user.

In certain non-limiting embodiments, the mapping can include transforming the data related to the one or more teeth of the pet to the heatmap using at least one of a tooth identification or a tooth location. The tooth identification can be based on at least one of a type of the pet product testing or a location at which the pet product testing occurs. In certain non-limiting embodiments, the method can include coloring, by the server, the heatmap representation based on the impact of the pet product on the one or more teeth of the pet. The coloring of the heatmap representation can be based on a breed or breed size of the pet used for the pet product testing. In certain non-limiting embodiments, the method can include determining a number of the one or more teeth to include within the heatmap representation based on the pet product being tested In certain non-limiting embodiments, the method can include starting, at the server, a timer for a duration of time. The method can also include monitoring, at the server, changes to the data related to the one or more teeth over the duration of the timer. In addition, the method can include mapping the changes onto the heatmap representation of the one or more teeth.

In certain non-limiting embodiments, an apparatus for processing data of a tested pet product can include at least one memory comprising computer program code, and at least one processor. The computer program code can be configured, when executed by the at least one processor, to cause the apparatus to collect, at the apparatus, data related to one or more teeth of a pet, the data results from the testing of the pet product. The computer program code can also be configured, when executed by the at least one processor, to cause the apparatus to map, by the apparatus, the data to a heatmap representation of the one or more teeth of the pet. The heatmap representation can illustrate a statistical analysis of the data. In addition, the computer program code can also be configured, when executed by the at least one processor, to cause the apparatus to determine based on the statistical analysis of the data illustrated in the heatmap representation an impact of the pet product on the one or more teeth of the pet.

According to certain embodiments a non-transitory computer-readable medium encoding instructions that, when executed in hardware perform a process. The process can include collecting, at the hardware, data related to one or more teeth of a pet, where the data results from the testing of the pet product. The process can also include mapping, by the hardware, the data to a heatmap representation of the one or more teeth of the pet. The heatmap representation can illustrate a statistical analysis of the data. In addition, the process can include determining based on the statistical analysis of the data illustrated in the heatmap representation an impact of the pet product on the one or more teeth of the pet.

An apparatus, in certain embodiments, can include a computer program product encoding instructions for processing data of a tested pet product according to a method. The method can include collecting, at a server, data related to one or more teeth of a pet, where the data results from the testing of the pet product. The method can also include mapping, by the server, the data to a heatmap representation of the one or more teeth of the pet. The heatmap representation can illustrate a statistical analysis of the data. In addition, the method can include determining based on the statistical analysis of the data illustrated in the heatmap representation an impact of the pet product on the one or more teeth of the pet. The data, for example, includes at least one of percentage of plaque or calculus on the one or more teeth or prevalence of periodontal disease for the one or more teeth.

It is to be understood that both the foregoing general description and the following detailed description are exemplary and are intended to provide further explanation of the disclosed subject matter claimed.

4. BRIEF DESCRIPTION OF THE DRAWINGS

FIG. 4 is a schematic representation of a user interface according to certain non-limiting embodiments;

5. DETAILED DESCRIPTION

Figure 1A:
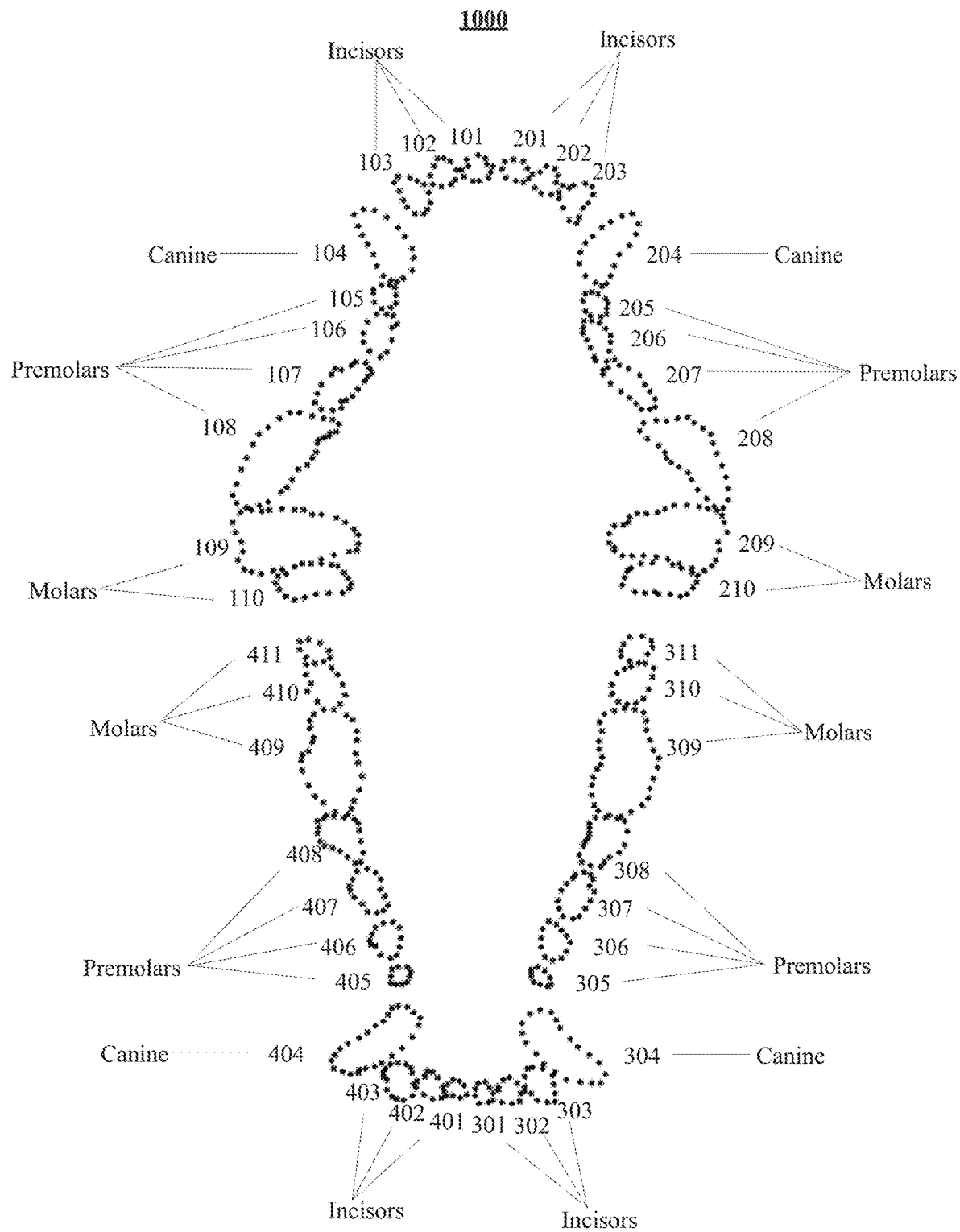
FIG. 1A illustrates a schematic representation according to certain non-limiting embodiments.

There remains a need in the pet product industry to better understand the results of pet product studies. Specifically, there remains a need for techniques that allow researchers of pet products to collect, analyze, and/or visualize results of studies over time, while preventing potential misinterpretation of the resulting data. The presently disclosed subject matter addresses these and other needs.

For clarity and not by way of limitation, this detailed description is divided into the following sub-portions:

5.1. Definitions;
5.2 Data of the one or more teeth;
5.3. Heatmap representations;
5.4. Flow diagram of method for pet product testing; and
5.5. System diagrams for pet product testing.

5.1. Definitions

The terms used in this specification generally have their ordinary meanings in the art, within the context of this disclosure and in the specific context where each term is used. Certain terms are discussed below, or elsewhere in the specification, to provide additional guidance in describing the compositions and methods of the disclosure and how to make and use them.

As used in the specification and the appended claims, the singular forms "a," "an" and "the" include plural referents unless the context clearly dictates otherwise. Thus, for example, reference to "a compound" includes mixtures of compounds.

The terms "animal" or "pet" as used in accordance with the present disclosure refers to domestic animals including, but not limited to, domestic dogs, domestic cats, horses, cows, ferrets, rabbits, pigs, rats, mice, gerbils, hamsters, goats, and the like. Domestic dogs and cats are particular non-limiting examples of pets. The term "animal" or "pet" as used in accordance with the present disclosure can further refer to wild animals, including, but not limited to bison, elk, deer, venison, duck, fowl, fish, and the like.

As used herein, the terms "comprises," "comprising," or any other variation thereof, are intended to cover a non-exclusive inclusion, such that a process, method, article, system, or apparatus that comprises a list of elements does not include only those elements but can include other elements not expressly listed or inherent to such process, method, article, or apparatus.

In the detailed description herein, references to "embodiment," "an embodiment," "one embodiment," "in various embodiments," "certain embodiments," "some embodiments," "other embodiments," "certain other embodiments," etc., indicate that the embodiment(s) described can include a particular feature, structure, or characteristic, but every embodiment might not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

The term "data" includes for example without limitation, any type of data related to one or more parts of the anatomy of a pet. In certain embodiments, the data can be any measurement of the health, or any other physical characteristic, of one or more teeth of a pet. For example, the data can include the percentage of plaque or calculus on one or more teeth, or the prevalence of periodontal disease or calculus for the one or more teeth.

The term "pet product" includes for example without limitation, any type of product that is designed, manufactured, or used by a pet. For example, the "pet product" can be a toy, chewable, food, or any other product that can come in contact with one or more teeth of the pet.

The term "statistical analysis of the data" includes for example without limitation, any type of statistical measure used to analyze or interpret data. For example, a mean, median, average, mode, or standard deviation of the set of data can be considered a "statistical analysis of the data." In other embodiments, any other statistical measurement of the data can be considered the "statistical analysis of the data."

The term "heatmap" includes for example without limitation, any form of map, chart, plot, or graph that can be used to illustrate or show data. For example, the "heatmap" can be colored. In one non-limiting example the "heatmap" can be shaped or drawn in the form of one or more teeth of a pet.

The phrase "impact of the pet product on the one or more teeth" refers to, for example without limitation, any effect the pet product has on the health of the one or more teeth of the pet. In a non-limiting example, impact can be a change to any physical characteristic of the one or more teeth, such as the shape, structure, or color of the one or more teeth. For example, the impact of the pet product can be percentage of plaque buildup or calculus on the one or more teeth or the prevalence of periodontal disease in a given pet.

The term "user" refers to, for example without limitation, any researcher, designer, product manufacturer, or any other individual, that is studying the impact of a pet product on one or more teeth of a pet. In certain non-limiting embodiments, the "user" can be any individual using or interacting with the terminal device, which can use or interact with the user interface and the heatmap representation being show thereon.

The term "terminal device" refers to, for example without limitation, a personal computer, laptop computer, workstation, mobile device, terminal device, or any other user equipment. In some non-limiting examples, the terminal device can include a graphical user interface used to display a heatmap representation to a user of the terminal device. In certain embodiments a web-based application can be installed on the user's terminal device. A user can view the heatmap using the web-based application.

5.2. Data of the One or More Teeth

In certain non-limiting embodiments, a server can collect data related to one or more teeth of a pet, where the data can result from the testing of the pet product. The test can be any type of test meant to analyze the impact of a pet product on one or more teeth of a pet. For example, a test can be simply feeding the pet a pet food product or allowing a pet to play with a chew toy for a finite amount of time. In some non-limiting embodiments, the test can involve providing the pet with a pet product. The pet can make contact with the pet product using one or more teeth. Data related to the health or any physical characteristic of the one or more teeth of the pet can then be collected. For example, a test can be initiated by a manufacturer, designer, or any researcher, in which a dog can be given a food product. The food product can be the pet product being tested. The dog can eat the pet food for a finite number of days, during or after which data related to one or more teeth of the dog is obtained. The obtained data can then be transmitted to a server, where the data can be collected and/or stored. The collected data reflects the results from the testing of the pet product.

An imaging sensor, or any other type of sensor, can be used to obtain the data related to one or more teeth of the pet. For example, any dental radiograph or x-ray of the teeth or jaw, such as a bite-wing x-ray, periapical x-ray, occlusal x-ray, extraoral x-ray, panoramic x-ray can be used. Three-dimensional imaging, such as dental computed tomography (CT), cone beam CT, or magnetic resonance imaging (MM) can be used, while in other examples two-dimensional imaging, such as a digital image, can be used. In another non-limiting example, a quantitative light-induced fluorescence camera can be used. While in the above embodiments an imaging sensor can be used to obtain data, in other non-limiting embodiments a non-imaging sensor can be used to obtain data related to any characteristic of the one or more teeth.

Once a given sensor obtains the data they can store the data in a memory device located within the sensor and/or transmit the data for storage to a memory device located outside the sensor. The given sensor can transmit the obtained data to a server, which can then collect the data related to the one or more teeth of a pet. In certain non-limiting embodiments, a centralized server can collect all of the data, while in other non-limiting embodiments the collection of data can be distributed to a plurality of servers. Each server can include one or more databases that store the collected information. When the centralized server collects all of the data, the data can be kept in one database or in multiple databases. The databases can include tags or identifiers describing characteristics of the collected data, such as the type of data collected, the sensor that obtained the data, and/or the breed or breed size of the pet for which the data was obtained. For example, if a pet product is tested on two breeds of pets, such as a dog and a cat, the collected data for the dog can be stored in a first database while the collected data for the cat can be stored in a second database. The first and second databases can include tags or identifiers indicating that the data included therein relates to dogs and cats, respectively.

In some non-limiting embodiments, rather than using an imaging or a non-imaging sensor, a visual exam of the one or more teeth can be performed by a researcher or a dentist. The visual exam, for example, can include a visual check with no instruments while the pet is conscious. Such a visual exam can involve an examination of at least some of the teeth. In yet another example, the visual exam can include a detailed exam using a dental probe while the pet is under anesthesia. Once the researcher and/or dentist performs the visual exam and scores the one or more teeth, they can input results of the exam into a terminal device. The terminal device can store and/or forward the data to a server, which can collect the data for the one or more teeth.

The data obtained can relate to any physical characteristic of one or more teeth of the dog. For example, the data can reflect the shape, structure, color, size, or any other characteristic, of the one or more teeth. The one or more teeth can include any part located on the tooth, as well as any part of the pet anatomy that surrounds or is located near the tooth, such as the pet's gums or gingiva. Parts located on the tooth, for example, can include at least a crown, root, enamel located on the crown, dentine, cementum, and/or periodontal ligament. Pet anatomy that surrounds or is located near the tooth can include, for example, at least the alveolar bone, lamina dura, attached gingiva, mucogingival junction, free gingiva, gingival sulcus, junctional epithelium, cemento-enamel junction, and/or interdental papilla. In one non-limiting example, data related to the one or more teeth of the pet can include data related to any of the above parts located on the tooth or any of the above pet anatomy that surrounds or is located near the tooth. In some other non-limiting embodiments, the data can be related to any other part of the pet anatomy, not related to the one or more teeth of the pet.

In certain non-limiting embodiments, the data of the one or more teeth can be a percentage of plaque or calculus, which is a type of plaque, formed on the crown or enamel of the one or more teeth. The plaque or calculus can be obtained using a quantitative light-induced fluorescence camera. The camera can obtain, capture, or sense the plaque or calculus and transmit the obtained data to a server. The server can then collect the data related to the one or more teeth of a pet. In some non-limiting embodiments, the quantitative light-induced fluorescence camera can transmit the obtained data to a terminal device, which can then forward, send, or retransmit the obtained data to a server.

In other non-limiting embodiments, the data of the one or more teeth can be the prevalence of periodontal disease. Prevalence of the periodontal disease, for example, can be the number, percentage, or proportion of teeth which are surrounded by gums and/or tissue that are infected with a periodontal disease. The prevalence of the periodontal disease can be detected using any imaging sensor or using a visual exam performed by a researcher, dentist, or veterinarian. When the prevalence of the periodontal disease is detected or obtained using a visual exam, the research and/or dentist can manually input the data into a terminal device. The terminal device or imaging sensor can then transmit the data of the one or more teeth to the server, where the data can be collected.

As discussed above, the data of the one or more teeth can be received at the server. The server can store the raw data received from the sensor and/or terminal device in one or more databases. In certain non-limiting embodiments, the server can perform statistical calculations of the collected data. For example, a researcher can test three separate pet products, referred to as X1, X2, and X3. The data collected for each of the pet products can be the percentage of plaque or calculus formed on the one or more teeth after using pet products X1, X2, and X3 for a finite amount of time. The server can then perform a statistical analysis of the raw data, meaning that the server can calculate statistics associated with the percentage of plaque or calculus. In one non-limiting example, the calculated statistics can be the mean and standard deviation ("Stdev") of the percentage of plaque or calculus formed on the one or more teeth for pet products X1, X2, and X3, as listed in table 1.

TABLE 1

Statistics of data for one or more teeth of products X1, X2, and X3

| Product | Mean | Stdev |
|---------|-------|-------|
| X1 | 0.401 | 0.329 |
| X2 | 0.436 | 0.324 |
| X3 | 0.595 | 0.362 |

As shown in Table 1, the mean percentage of plaque or calculus of the one or more teeth for product X1, X2, and X3 can be 0.401%, 0.436%, and 0.595%, while the standard deviation can be 0.329%, 0.324%, and 0.362%, respectively. From the statistical analysis of the data shown in Table 1, it appears that X3 has the worst percentage of plaque or calculus, while X1 has the best percentage of plaque or calculus.

5.3. Heatmap Representation

Figure 1B:
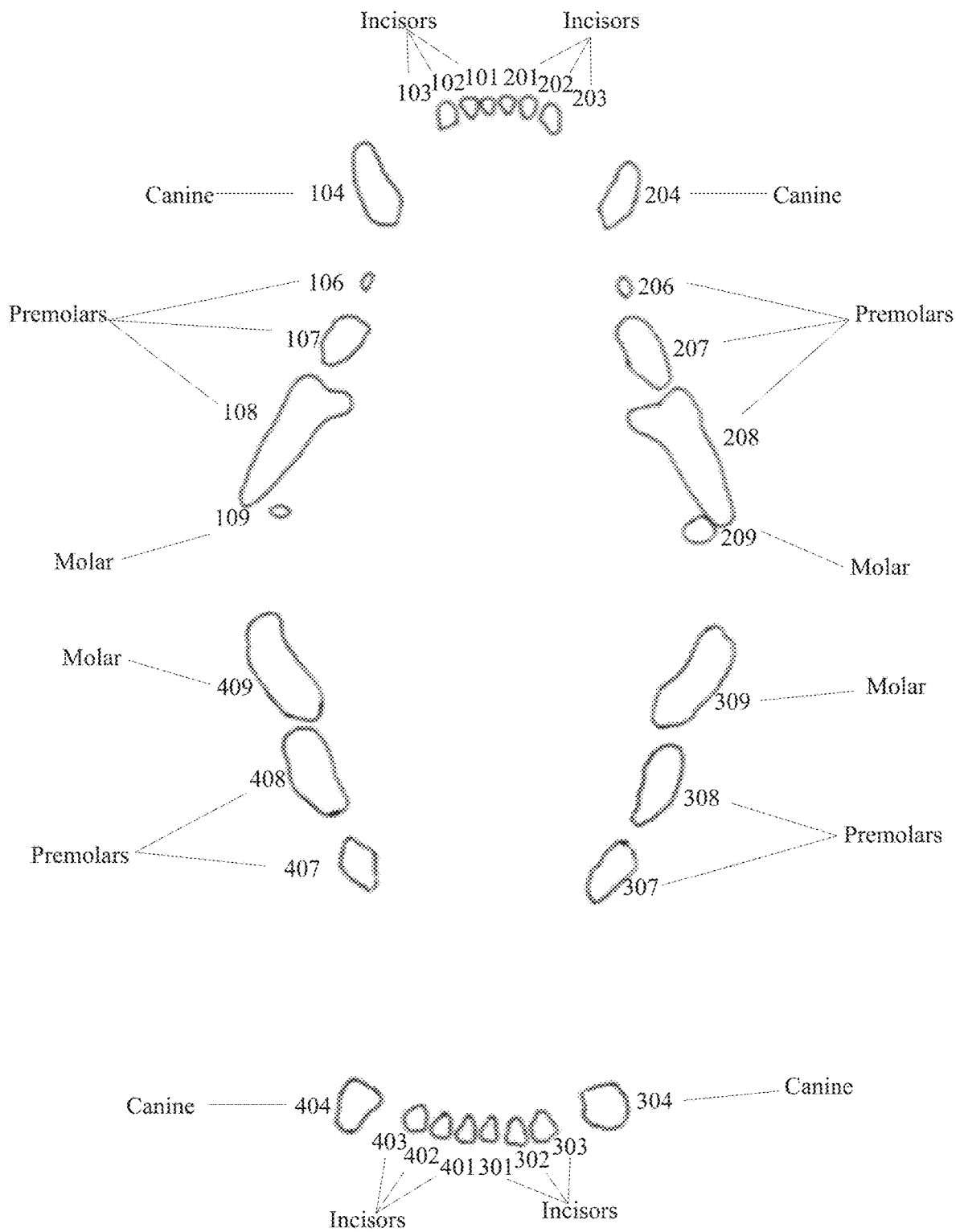
FIG. 1B illustrates a schematic representation according to certain non-limiting embodiments.

In certain non-limiting embodiments, instead of showing the statistical analysis of the data in a simple table, such as Table 1, it can be beneficial to map the collected data to a heatmap representation of the one or more teeth. The heatmap representation can be a graphical representation of data, or statistical analysis of data, which takes the form of a part of the pet anatomy, such as one or more teeth of the pet. FIG. 1A illustrates a schematic representation according to certain non-limiting embodiments. In particular, FIG. 1A illustrates a heatmap representation that includes the teeth on the upper and lower jaw 1000 of a dog. In other embodiments, however, the schematic representation can illustrate the jaw of any other pet, such as a cat, as shown in FIG. 1B.

Teeth 101-103, 201-203, 301-303, and 401-403 can be referred to incisors located in the pet's upper and lower front jaw, as shown in FIG. 1A. Incisors, for example, can be used for cutting, scooping, grooming, and/or picking up objects. As shown in FIG. 1A, incisors are generally small, single-rooted teeth, which can become mobile when affected by periodontal disease. FIG. 1A also illustrates canines 104, 204, 304, and 404. Canines 104, 204, 304, and 404, for example, can be used for holding prey, display, slashing, and/or tearing. Canines 104, 204, 304, and 404 also form a cradle for the tongue of the pet. Premolars 105-108, 205-208, 305-308, and 405-408, are located behind the canine, and can be used for holding, carrying, and/or breaking food into smaller pieces. Healthy premolars generally show a pinking shear appearance, meaning that the tip of the upper tooth of the premolars point into an interdental space of the lower jaw. If the premolars do not appear as a pinking shear, this can indicate a bite defect such as mandibular prognathism or brachygnathism. In certain non-limiting embodiments, therefore, data can be collected related to the pinking shear appearance of premolars 105-108, 205-208, 305-308, 405-408. Molars 109, 110, 209, 210, 309-311, and 409-411 shown in FIG. 1A are located behind the premolars. Molars are generally shaped with flat occlusal surfaces that can be used for grinding food into small pieces.

In some embodiment a tooth identification and/or a tooth location can be assigned to the one or more teeth. In one non-limiting example, the tooth identification can be designated using the modified Tridian system, as shown in FIGS. 1A and 1B. The modified Tridian system uses a three-digit number to identify a given tooth across different pets. The first digit of the tooth identification represents a quadrant in which the tooth is located. A mouth can be divided into four quadrants, with each of upper jaw and lower jaw including two of the four quadrants. The first quadrant can be referred to as the right upper permanent, the second quadrant can be referred to as the left upper permanent, the third quadrant can be referred to as the left lower permanent, and the fourth quadrant can be referred to as the right lower permanent. The second and third digits can denote the tooth position within the quadrant, with the sequence starting at the jaw midline. Under the modified Tridian system, second and third digits 01-03 can represent incisors, second and third digits 04 can represent canines, second and third digits 05-08 can represent the premolars, and second and third digits 09-11 can represent the molars. For example, tooth identification 103 can represent the third incisor from the midline of the right upper jaw. In some non-limiting examples, the identification can be unique to each tooth. The tooth identification can be kept in a tooth identification file, as shown in Table 2.

TABLE 2

Tooth identification file

| | Shape ID | Tooth ID |
|---|---|---|
| 1 | 1 | 101-D |
| 2 | 2 | 102-D |
| 3 | 3 | 103-D |
| 4 | 4 | 104-D |
| 5 | 5 | 105-D |
| 6 | 6 | 106-D |

The tooth location assigned to the one or more teeth can be in the form of a coordinate on the two-dimensional heatmap representation of the one or more teeth. For example, teeth located on the heatmap representation can be assigned a horizontal coordinate, referred to as X, and a vertical coordinate, referred to as Y, designating the location of the tooth within the two-dimensional heatmap representation. The tooth location can be kept in a tooth location file, which can be in a separate database or location within the server from the tooth identification file, as shown in Table 3.

TABLE 3

Tooth location file

| Shape ID | Part ID | X | Y |
|---|---|---|---|
| 1 | 1 | 1 | 48.72139 ... | 93.494705 |
| 2 | 1 | 1 | 49.39434 ... | 93.64599 ... |
| 3 | 1 | 1 | 49.52893 ... | 92.88956 ... |
| 4 | 1 | 1 | 49.66352 ... | 92.13313 ... |
| 5 | 1 | 1 | 49.39434 ... | 91.376702 |
| 6 | 1 | 1 | 49.12516 ... | 90.77155 ... |
| 7 | 1 | 1 | 48.72139 ... | 91.98184 ... |
| 8 | 1 | 1 | 48.45222 ... | 92.88956 ... |
| 9 | 1 | 1 | 48.72139 ... | 93.494705 |
| 10 | 2 | 1 | 47.54468 ... | 92.88956 ... |

As shown in the above Tables 2 and 3, both the data identification file and the data location file can include a shape identification. When mapping data related to the one or more teeth to a heatmap representation, the server can utilize at least one of Tables 2 and/or 3. In certain non-limiting examples, in which both Tables 2 and 3 are used, the shape identification included in each table can be used to combine the information in Tables 2 and 3 to determine the XY coordinates for a given tooth identification. Table 3, therefore, can identify the X and Y coordinates on the graph, while Table 2 can identify the tooth identification of the tooth in a given XY coordinate. In certain non-limiting embodiments the heatmap representation can be a three-dimensional representation. In such embodiments, the data location file can include X, Y, and Z coordinates, which Z representing the depth of a given tooth.

In some non-limiting examples, a researcher or designer can use a customized graphics tool to generate the heatmap representation. The customized graphics tool can allow for the use of Table 2, Table 3, and/or any other table or data file to map the heatmap representation. In other words, the mapping of the data can include transforming the data related to the one or more teeth of the pet to the heatmap using at least one of a tooth identification or a tooth location. In addition, or as an alternative, the customized graphics tool can allow a user to select how the teeth are label and/or which table column includes the label. The customized graphics tool can then match the selected label for the teeth with any stored information, to which the server has access, and generate one or more columns of data. The generated one or more columns of data, for example, can resemble the tooth identification file shown in Table 2.

FIG. 1B illustrates a schematic representation according to certain non-limiting embodiments. In particular, FIG. 1B illustrates a heatmap representation that includes the teeth on jaw 1100 of a cat. As shown in FIG. 1B, the upper cat jar includes molars 109 and 209, premolars 106-108 and 206-208, canines 104 and 204, and incisors 101-103 and 201-203. The lower cat jar includes molars 309 and 409, premolars 307, 308 407, 408, canines 304 and 404, and incisors 301-303 and 401-403. The above description related to FIG. 1A, and the mapping of the heatmap representation illustrated therein, can also apply to FIG. 1B, and the mapping of the heatmap representations illustrated therein.

Figure 2:
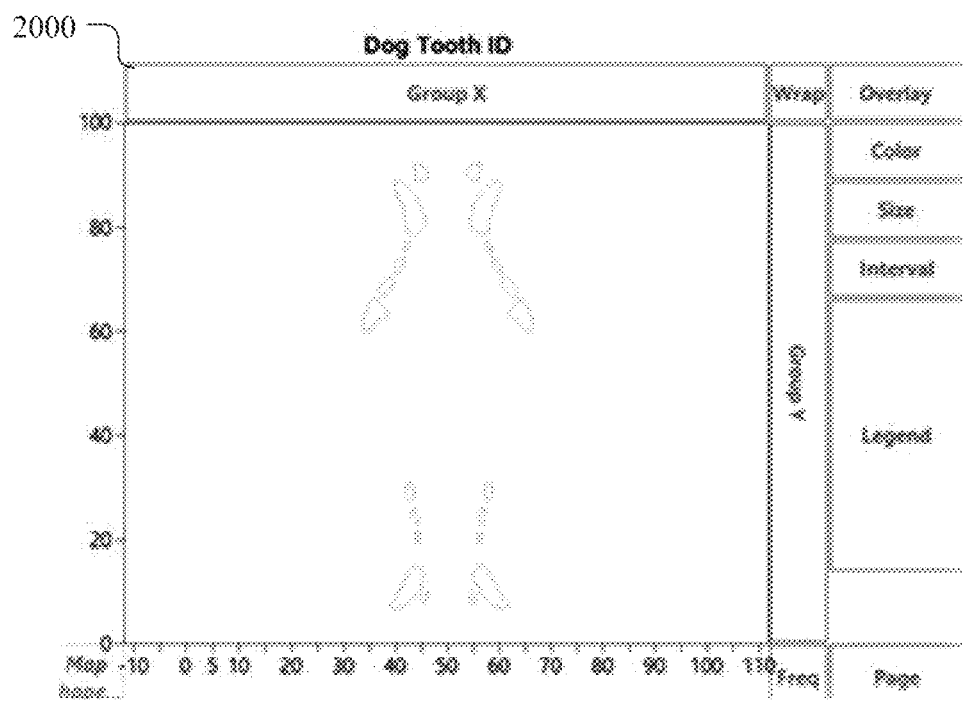
FIG. 2 illustrates a schematic representation according to certain non-limiting embodiments.
Figure 3:
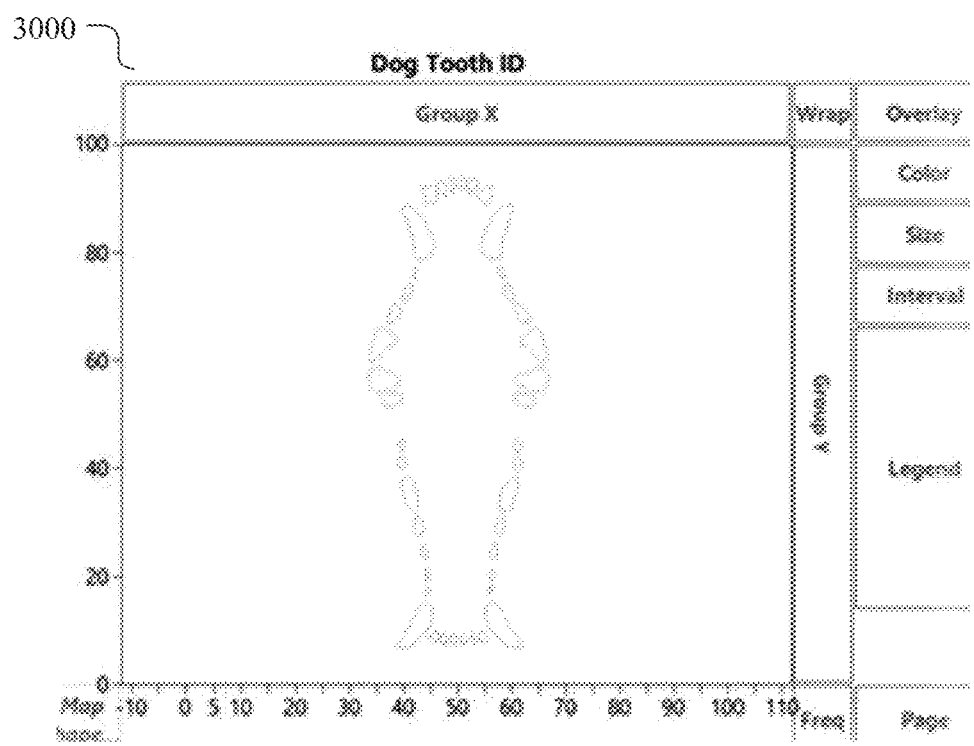
FIG. 3 illustrates a schematic representation according to certain non-limiting embodiments.

FIGS. 2 and 3 illustrate a schematic representation according to certain non-limiting embodiments. In particular, FIGS. 2 and 3 illustrate heatmap representations of one or more teeth of a pet. In certain non-limiting embodiments, as shown in FIG. 2, the heatmap representation 2000 can show the one or more teeth for which data was collected. In other words, the heatmap representation can selectively show those one or more teeth on which the impact of a pet product was tested. The one or more teeth of FIG. 2 are illustrated in an XY, cartesian coordinate plane. On the other hand, FIG. 3 illustrates a heatmap representation 3000 of all the teeth of the pet, even those teeth for which data was not collected. The one or more teeth of FIG. 3 are similarly shown in an XY, cartesian coordinate plane. A user, in one non-limiting example, can select whether to use heatmap representation 2000 showing those one or more teeth for which data was collected, or heatmap representation 3000 showing all of the teeth of a pet. In other non-limiting embodiments, the user can select a hybrid of heatmap representations 2000, 3000, showing one or more teeth of a pet for which data was not collected, but not showing all of the teeth of a pet.

Figure 4:
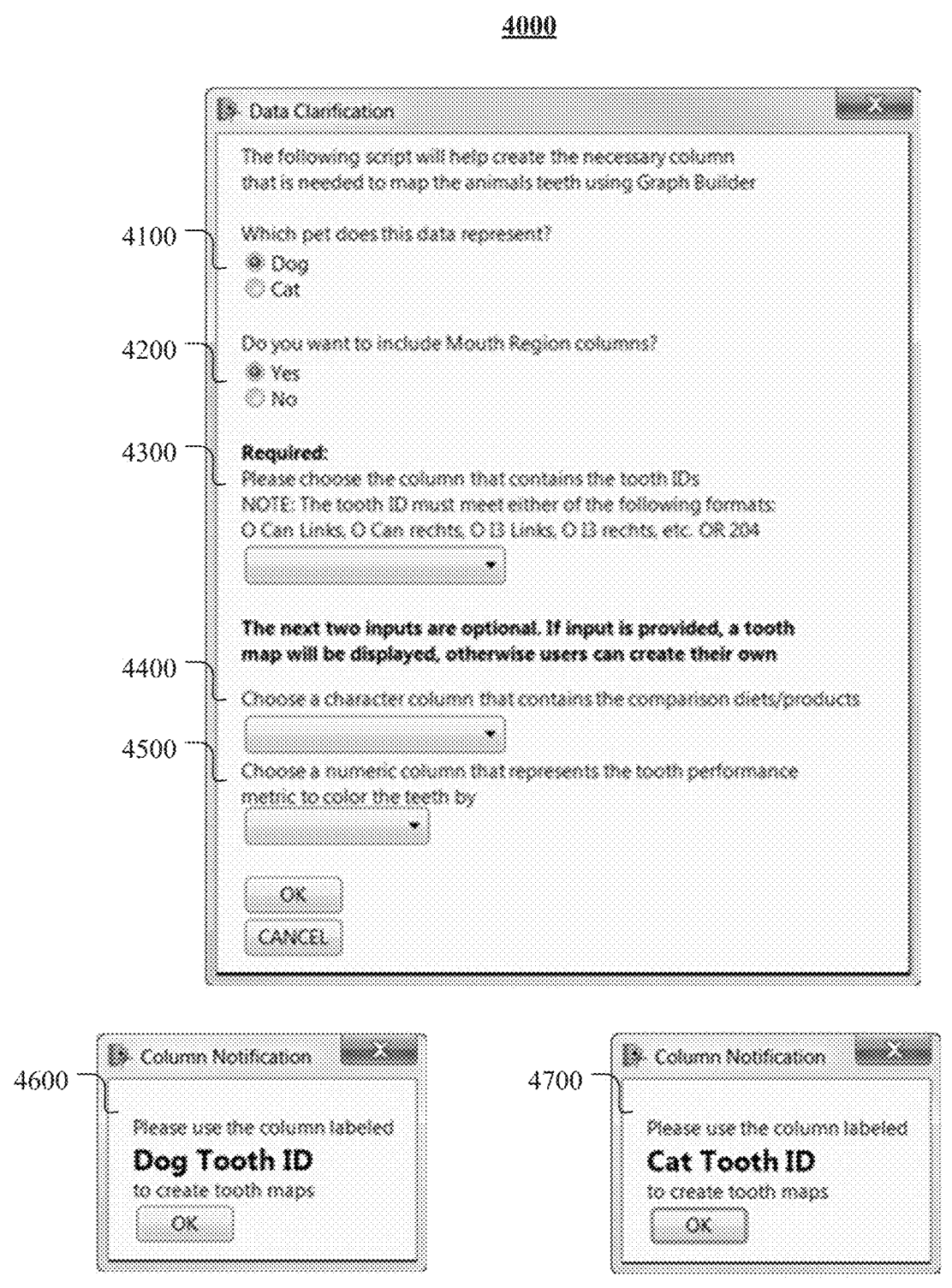

FIG. 4 is a schematic representation of a user interface according to certain non-limiting embodiments. The user interface can be part of a terminal device used by a researcher or designer testing a given pet product. In particular, FIG. 4 illustrates a user interface 4000 that can provide a user with one or more display options for the heatmap representation. The heatmap representation can be changed based on the one or more display options selected by the user. In other words, user interface 4000 can help a researcher or designer map a heatmap representation of one or more teeth of the pet. In certain non-limiting embodiments, the user interface can help map the one or more teeth of the pet to the proper location within a heatmap. For example, the user interface can prompt, request, or ask the user to provide which pet the data represents 4100, such as cat, dog, or any other pet. The user interface can also ask the user if they would like to include a mouth region column 4200. As explained above with regarding to FIG. 1A, a dog can have four mouth regions, a right upper permanent, a left upper permanent, a right lower permanent, and/or a left lower permanent.

In 4300, the user can be asked or prompted to provide a tooth identification format. In certain non-limiting embodiments, the user can select the column within a data file and/or table that includes the tooth identification. The tooth identification can be based on a type of test run, meaning the type of test used to collect the data, or where the test was performed, meaning the location of the one or more tooth tested or the physical location of the pet when the test was performed. In one non-limiting example, therefore, different tooth identifications can indicate different types of tests performed to collect the data and/or different locations of the one or more teeth being tested. In the user interface shown in FIG. 4, the column options, provided to the user can be canine ("Can") left, Can right, premolar ("PM") 1/PM2/PM3 left, PM1/PM2/PM3 right, incisor ("I") I3 left, and/or I3 right. On the other hand, in certain non-limiting embodiments instead of selecting the above column options, which are identified using a description, a numerical value of the column can be selected, such as, for example, column 204.

Using the above information selected or inputted by the user, a column of tooth labels can be created that corresponds to the tooth map files. At least one of the tooth label columns, or any column, or combination of columns, in the tooth identification file and/or tooth location file can be used to map the data to a heatmap representation of the one or more teeth of the pet. In certain non-limiting embodiments, one or more additional inputs can be selected by the user. For example, as shown in FIG. 4 the user can choose a character column 4400 that contains the comparison diet or products, and/or a numeric column 4500 that represents the tooth performance metric used to color the one or more teeth of the heatmap representation. After the column is selected or chosen, a separate notification window can be displayed on the user interface notifying the user of the column name that includes the new column name for the mapping. For example, when a user selects a dog as input 4100, notification window 4600 can be shown on the user interface of the terminal device notifying the user that column labeled Dog Teeth ID has been created to be used for the mapping. In another example, when a user selects cat as input 4100, notification window 4700 can be shown on the user interface of the terminal device notifying the user that column labeled Cat Teeth ID has been created to be used for the mapping. Dog Teeth ID 4600 and/or Cat Teeth ID 4700, for example, can used by the customized graphics tool to generate the heatmap representation.

Any of the above columns can be used to generate or map the heatmap representation of the one or more teeth. In other words, the mapping can include transforming the data related to the one or more teeth of the pet to the heatmap representation using any of the above information or columns, such as, for example, at least one of the tooth identification and/or the tooth location. The tooth identification can be based on at least one of a type of the pet product testing or a location at which the pet product testing occurs.

After the heatmap representation is mapped or generated, the user can further manipulate the representation. The manipulation can occur before or after the heatmap representation is displayed on the graphical user interface of the terminal device. For example, in certain non-limiting embodiments, a user can be provided with one or more display options for the heatmap representation at the user interface of the terminal device. The display options, for example, can be the colors used for the heatmap representation of the one or more colors. Based on the one or more display options selected by the user, the server can change the heatmap representation.

Figure 5A:
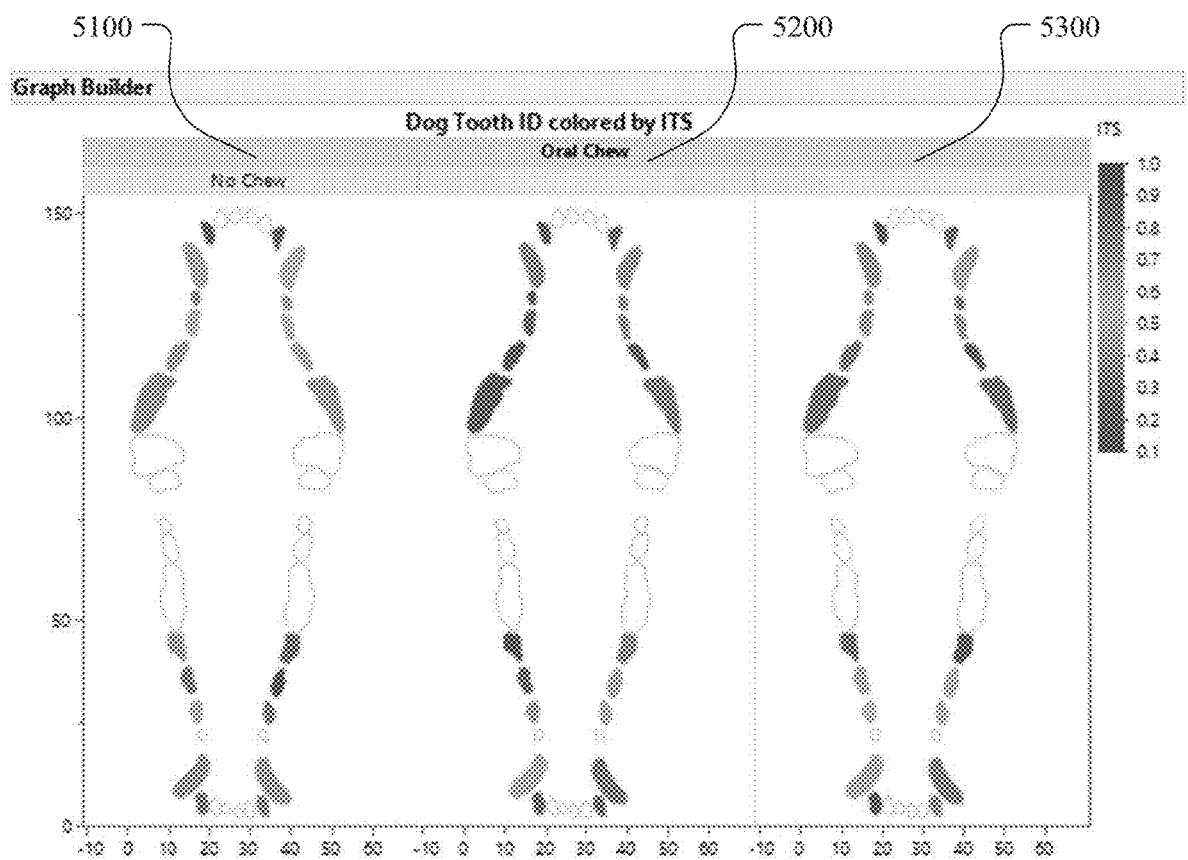
FIG. 5A illustrates a schematic representation of data results according to certain non-limiting embodiments.

FIG. 5A illustrates a schematic representation of data results according to certain non-limiting embodiments. In particular, FIG. 5A illustrates a mapping of data to a heatmap representation of the one or more teeth of a pet, such as a dog, shown on a user interface 5000 of a terminal device. The heatmap representation can illustrate a statistical analysis of the data. In some non-limiting embodiments, any statistical analysis software can be used to help generate the heatmap representation.

In certain non-limiting embodiments, the one or more teeth can be colored based on the values in the data. For example, the color can be based on the statistical analysis of the data. The statistical analysis of the data can include any type of statistical measure used to analyze or interpret data, such as a mean, median, average, mode, or standard deviation of the data. The coloring shown in FIG. 5A, for example, reflects the mean value of plaque or calculus on the one or more teeth of the tested pet product. A mean of 1.0 can be represented by the color red, while a mean of 0.0 can be represented by the color blue, with values therebetween being represented by shades of blue, grey, and red. The heatmap representation can include a default coloring and/or statistical analysis. For example, the default coloring can range from blue to red, while the default statistical analysis of the data can be the mean of the data. The default coloring and/or statistical analysis can be changed or adjusted by the user. The coloring, in one non-limiting example, can be changed to a customer built gradient based on the user's preference. In some non-limiting embodiments, the coloring can be based on a species, breed, or breed size of the pet used for the pet product testing. Breed size, for example, can be categorized as small, medium, and large. For example, for statistical analysis of data related to a dog the colors illustrated in the heatmap representation can range from red to blue, while for statistical analysis of data related to a cat the colors illustrated in the heatmap representation can range from yellow to red. In addition, or as an alternative to changing or adjusting the coloring of the heat map, a user can change or adjust the color theme, lightness range, scale type, range type, minimum, center, and/or maximum. These changes/adjustments can be presented as display options for the user to choose or select.

In some non-limiting embodiments, the heatmap representation can include one or more pet jaws, each including one or more teeth. Each of the one or more pet jaws can be a heatmap representation of an impact of the pet product on the one or more teeth of the pet. FIG. 5A, for examples, illustrates data related to one or more teeth for two different pet products, as well as data of one or more teeth without any pet products, which can be used as a control or baseline for the testing of the other pet products. In one non-limiting example, FIG. 5A can illustrate data related to a pet product, such as an oral chew, for one or more teeth of a pet can be collected by a server. An oral chew can be, for example, a chew toy or pet food. Heatmap representation 5100 can show data related to one or more teeth of a pet with no chew product being used by the pet. Those teeth that do not have any coloring can be those teeth that were not included as part of the test, or for which no data was collected. While heatmap representation 5100 can be used as a control or baseline heatmap, heatmap representation 5200 can be directed to data related to a first dental product, while heatmap representation 5300 can be directed to data related to a second dental product.

As described above, user interface 5000 can include three heatmap representations 5100, 5200, and 5300 illustrating a statistical analysis of the data. In particular, heatmap representation 5100 illustrates a baseline mean plaque percentage or calculus on the one or more teeth, without any pet product. Heatmap representations 5200 and 5300 illustrate the mean plaque percentage or calculus on the one or more teeth, ranging from a value of 0 to a value of 1. A value of 0 represents 0.0% plaque and the value of 1 represents 100% plaque. Heatmap representation 5200, therefore, illustrates the mean plaque on the one or more teeth for the tested first dental product, while heatmap representation 5300 illustrates the mean plaque on the one or more teeth for the tested second dental product.

Heatmap representations 5200 and 5300 can then be compared. Heatmap representation 5200 appears to be bluer than heatmap representation 5300, meaning that first dental product lowers plaque percentage more than the second dental product, or leads to a lower plaque percentage than the second dental product. Based on the comparison between heatmap representation 5200 and 5300, and heatmap representation 5200 being bluer than heatmap representation 5300, a researcher or user can choose a first dental product over the second dental product. In other words, the first dental product can be deemed the preferred product and chosen over the second dental product.

In certain non-limiting embodiments, the heatmap representation can be interactive, allowing the user to point to or click on one or more teeth on the heatmap representation to obtain additional data, such as the mean plaque for the one or more teeth. When the user points to or clicks on one or more teeth, additional information can be displayed on the user interface and/or a separate window can be opened or access that includes the additional information. Additional information, for example, can include the tooth identification, mean plaque for the given tooth, and/or any other data related to the tooth.

In some-non limiting embodiments, the heatmap representation can determine changes to data related to the one or more teeth over a finite period of time. The finite period of time can be determined based on a timer, which can be kept at the server and/or terminal device. The timer can be started when the server and/or terminal device begins to collect data related to the one or more teeth. Once the timer expires, the server and/or terminal device can stop collecting data related to the one or more teeth. During the duration of the timer, the server and/or terminal device can monitor changes to the data of the one or more teeth. The monitored changes to the data can then be mapped to a heatmap representation, which can be used to choose or select a pet product.

Figure 5B:
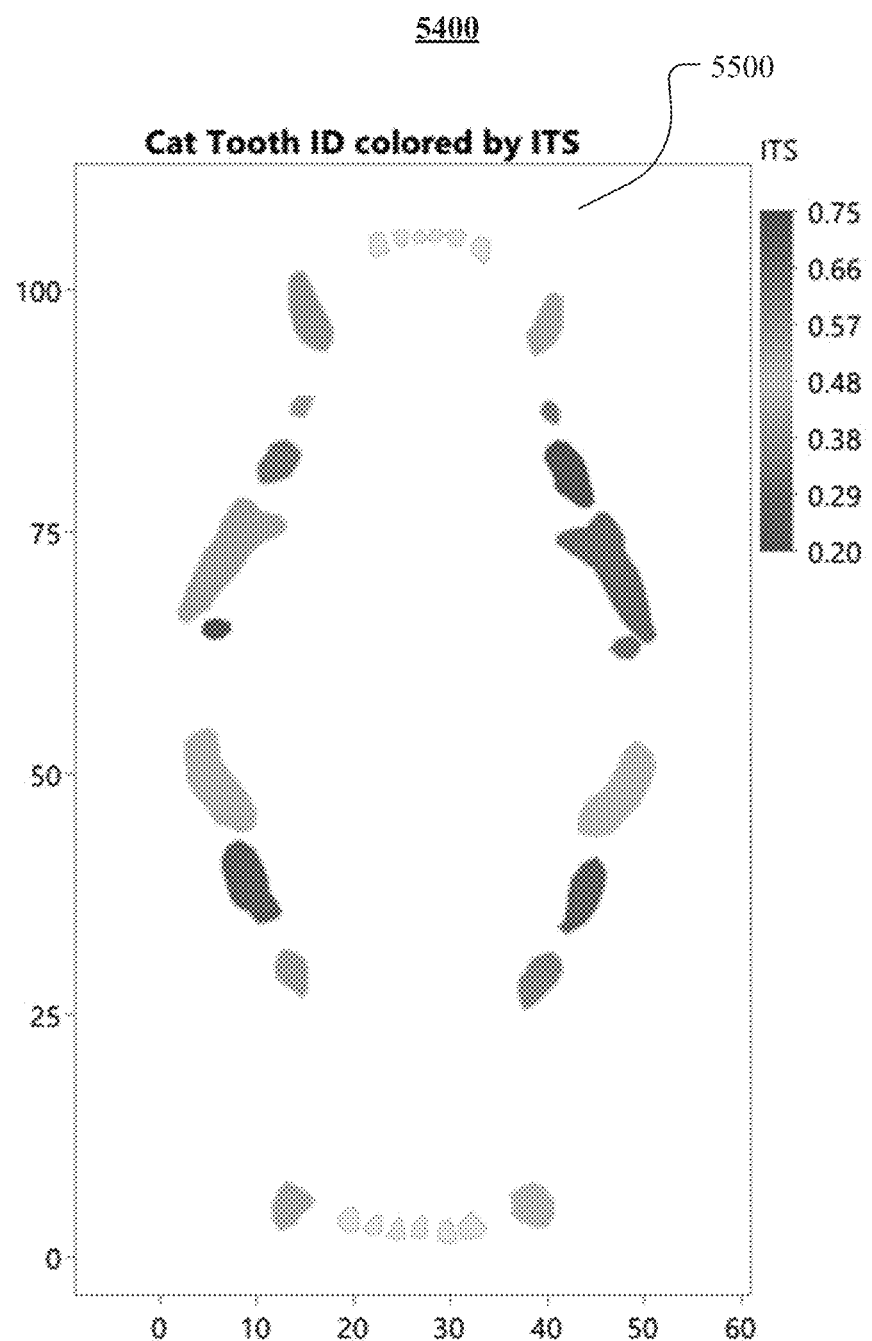
FIG. 5B illustrates a schematic representation of data results according to certain non-limiting embodiments.

FIG. 5B illustrates a schematic representation of data results according to certain non-limiting embodiments. In particular, FIG. 5B illustrates a mapping of data to a heatmap representation of the one or more teeth of a pet, such as a cat, shown on a user interface 5400 of a terminal device. In one non-limiting example, FIG. 5B illustrates a heatmap representation 5500 of one or more teeth of a cat testing a dental product. The heatmap representation can illustrate a statistical analysis of the data, such as a mean percentage of plaque or calculus formed on the crown or enamel of the one or more teeth of the cat. The percentage of plaque or calculus on the one or more teeth of the cat can range from 20%, represented by 0.20, to 75%, represented by 0.75. A plaque or calculus percentage of 75% can be shown in a red color on the heatmap representation, while a plaque or calculus percentage of 20% can be shown in a blue color on the heatmap representation. The one or more teeth illustrated in heatmap representation 5500 have a plaque or calculus percentage ranging between 20% to 75%.

Mapping data related to the pet product to a heatmap representation can provide significant advantages. Some non-limiting embodiments allow for visualizing the results in the manner provides another dimension for researchers to help provide context of how one or more pet products impact the one or more teeth. For example, a user can split up the coloring according to cats and/or dogs to perform an observational study on how the pet product was consumed by each pet. This can provide further context beyond merely having summarized data, and improve how users choose pet products without requiring additional statistical analysis and/or data to be collected. In other words, using the heatmap representation as described above can allow users to choose a pet product with a reduced number of calculations performed by the server and/or the terminal device. The reduced number of calculations will similarly reduce the resources needed to process the calculation, thereby providing a substantial reduction to the number of network and device resources being used to choose a pet product. Lowering the number of resources will improve the functionality of the server and/or terminal device used to perform the study of the pet product.

In certain embodiments, the heatmap representation can be used to help an owner, veterinarian, or researcher determine a care pathway for a pet. Care pathway can be a plan for treating the health of a pet, and can include, for example, targeted tooth brushing or diet adjustment. In one example, after scoring and identifying gingivitis or gum disease hotspots on one or more teeth, a veterinarian can use the heatmap to explain to the owner which teeth they need to target via tooth brushing. The heatmap can then be used as a monitoring tool to determine changes over time. In another example, a conscious scoring method, such as quantitative light-induced fluorescence ("QLF") can be used. The outputted data of the conscious scoring method can be visualized using one or more heatmaps. The heatmaps, for example, can be visualized on a terminal device or a web-based application in the terminal device. Based on the heatmaps a user can determine the efficacy of a given care pathway for a pet.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

5.4. Flow Diagram of Method for Pet Product Testing

Figure 6:
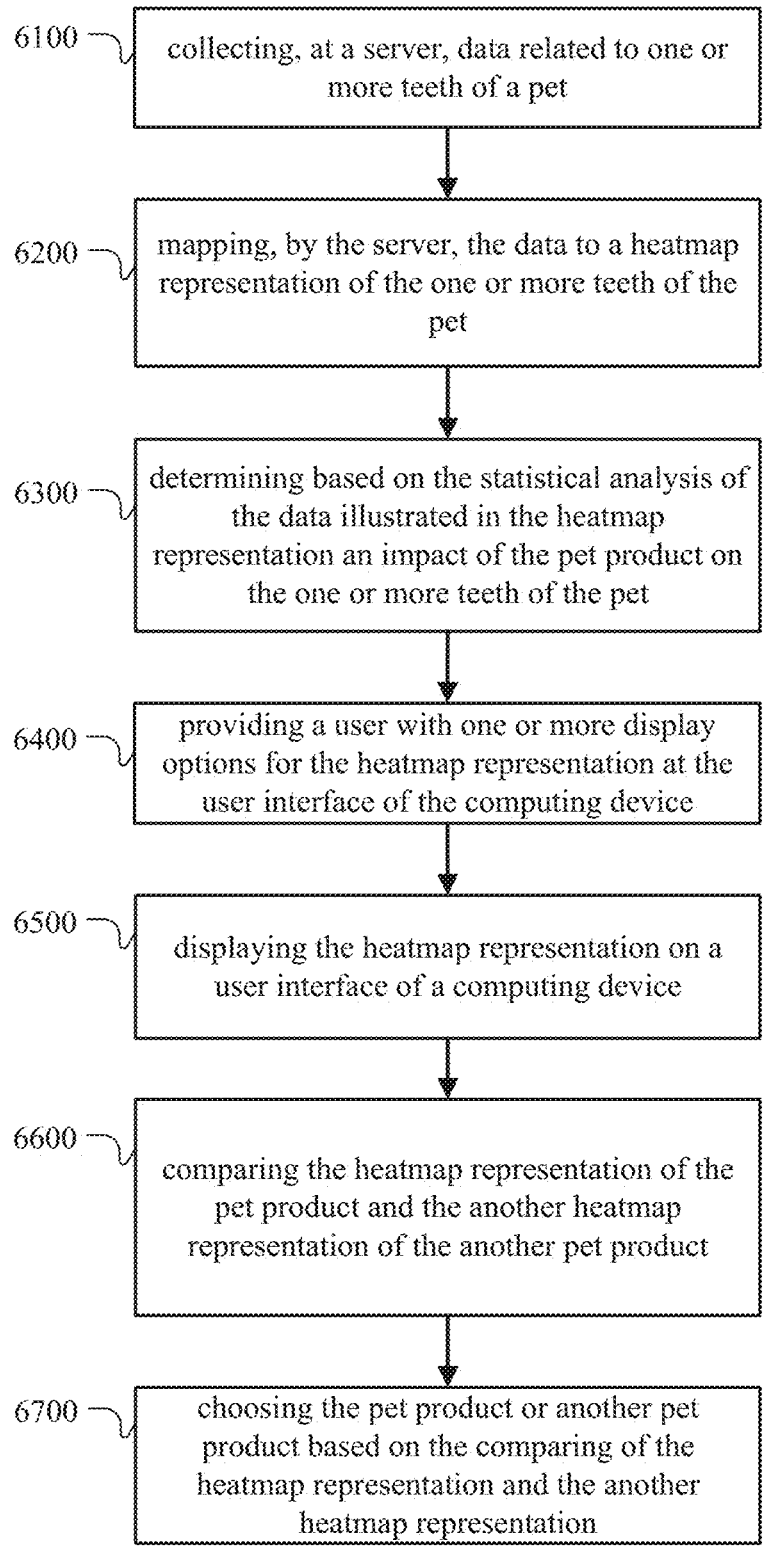
FIG. 6 illustrates a flow diagram according to certain non-limiting embodiments.

FIG. 6 illustrates a flow diagram according to certain non-limiting embodiments. In particular, FIG. 6 illustrates a method 6000 performed by a server and/or a terminal device for testing of a pet product. In step 6100, the server or the terminal device can collect data related to one or more teeth of a pet. The data results from the testing of the pet products. For example, the data can include at least one of percentage of plaque or calculus on the one or more teeth or prevalence of periodontal disease for the one or more teeth. In step 6200, the server or the terminal device can map the data to a heatmap representation of the one or more teeth of the pet, as shown in FIGS. 5A and 5B. The heatmap representation can illustrate a statistical analysis of the data. The server can determine a number of the one or more teeth to include within the heatmap representation based on the pet product being tested. As shown in FIG. 2, less than all of the one or more teeth of the pet are included in the heatmap representation, while in FIG. 3 all of the one or more teeth of the pet are included in the heatmap representation.

In certain non-limiting embodiments, a timer can start in the server for a duration of time. The server can then monitor changes to the data related to the one or more teeth over the duration of the timer. The mapping of the heatmap representation of the one or more teeth can be changed based on the monitored changes. The mapping can include transforming the data related to the one or more teeth of the pet to the heatmap using at least one of a tooth identification or a tooth location. The tooth identification can be based on at least one of a type of the pet product testing or a location at which the pet product testing occurs. As shown in FIGS. 5A and 5B, the heatmap representation can be colored, by the server or the terminal device, based on the statistical analysis of the data for the one or more teeth of the pet. The coloring of the heatmap can be based on a species, breed, or breed size of the pet used for the pet product testing.

Based on the statistical analysis of the data in the heatmap representation, an impact of the pet product on the one or more teeth of the pet can be determined, as shown in step 6300. In step 6400, a user can be provided with one or more display options for the heatmap representation at the user interface of the terminal device. After one or more display options are selected by the user, the options can be transmitted to the server. The server can receive the selection, and the heatmap representation can be changed based on the one or more display options selected by the user. As shown in step 6500, the heatmap representation can be displayed on a user interface of the terminal device. In certain non-limiting embodiments, the server or apparatus can transmit the heatmap representation from to the terminal device, where the heatmap representation can be displayed on a user interface.

The server or terminal device can collect data related to the one or more teeth of the pet, where the data results from the testing of another pet product. The sever or terminal device can then map the data to the another heatmap representation of the one or more teeth of the pet. As shown in FIGS. 5A and 5B, both the heatmap representation and the another heatmap representation can be displayed in the user interface of the terminal device. In step 6600, the heatmap representation of the pet product can be compared to the another heatmap representation of the another pet product. Based on the comparison of the heatmap representation and the another heatmap representation, the pet produce or the another pet product can be chosen, as shown in step 6700. The chosen pet product or the another pet product can be referred to as a preferred product. For example, the chosen preferred product can exhibit a lower mean percentage of plaque or a lower mean prevalence of periodontal disease in the one or more teeth.

5.5. System Diagrams for Pet Product Testing

Figure 7:
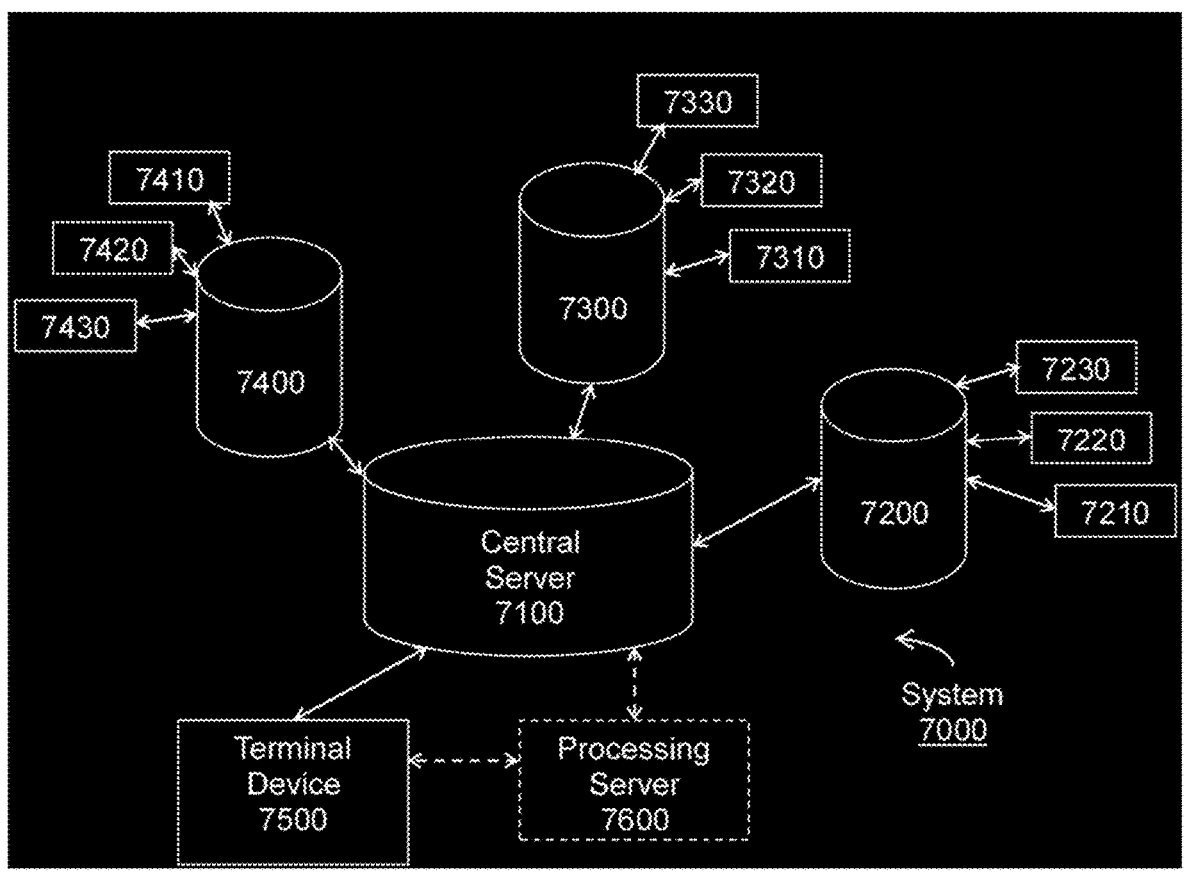
FIG. 7 illustrates a diagram of a system according to certain non-limiting embodiments.

FIG. 7 illustrates a diagram of a system 7000 according to certain non-limiting embodiments. In particular, certain non-limiting embodiments can include distributed resources that can include one or more servers configured to process data of a tested pet product. For example, in one embodiment of the disclosed subject matter, a monitoring system 7000 is provided. Monitoring system 7000 can comprise one or more components, such as one or more servers, which can collect data related to one or more teeth of a pet, map the data to a heatmap representation, and determine an impact of the pet product on the one or more teeth of the pet. With reference to the embodiment of FIG. 7, for purposes of illustration and not limitation, the monitoring component can comprise a central server 7100, which collects data from one or more individual servers 7200, 7300, 7400. In certain embodiments, the central server 7100 can include a server computer, a desktop computer, a laptop computer, a cloud-based computing device, among other available computing devices. In some embodiments, the central server 7100 can comprise multiple computers.

Furthermore, in certain embodiments, the one or more individual servers 7200, 7300, 7400 can include a server computer, a desktop computer, a laptop computer, a cloud-based computing device, among other available computing devices. In this non-limiting embodiment, the individual servers 7200, 7300, 7400 can collect data from the one or more distributed resources 7210-7230, 7310-7330, and 7410-7430, respectively, used for processing data of a tested pet product. Distributed resources 7210-7230, 7310-7330, and/or 7410-7430 can be any imaging or non-imaging sensor. In addition to static data, such as but not limited to resource identification information including resource or host name, processor architecture (i.e., number of cores), and/or location of resource, the data collected from the resources can include, among other measurable information, memory usage and/or availability (GB), CPU speed (MHz), and start and end hour such as the time when the resource is available or running.

FIG. 7 illustrates a diagram of a system 7000 according to certain non-limiting embodiments. In particular, certain non-limiting embodiments can include distributed resources that can include one or more servers configured to process data of a tested pet product. For example, in one embodiment of the disclosed subject matter, a monitoring system 7000 is provided. Monitoring system 7000 can comprise one or more components, such as one or more servers, which can collect data related to one or more teeth of a pet, map the data to a heatmap representation, and determine an impact of the pet product on the one or more teeth of the pet. With reference to the embodiment of FIG. 7, for purposes of illustration and not limitation, the monitoring component can comprise a central server 7100, which collects data from one or more individual servers 7200, 7300, 7400. In certain embodiments, the central server 7100 can include a server computer, a desktop computer, a laptop computer, a cloud-based computing device, among other available computing devices. In some embodiments, the central server 7100 can comprise multiple computers. Furthermore, in certain embodiments, the one or more individual servers 7200, 7300, 7400 can include a server computer, a desktop computer, a laptop computer, a cloud-based computing device, among other available computing devices. In this non-limiting embodiment, the individual servers 7200, 7300, 7400 can collect data from the one or more distributed resources 7210-7230, 7310-7330, and 7410-7430, respectively, used for processing data of a tested pet product. Distributed resources 7210-7230, 7310-7330, and/or 7410-7430 can be any imaging or non-imaging sensor. In addition to static data, such as but not limited to resource identification information including resource or host name, processor architecture (i.e., number of cores), and/or location of resource, the data collected from the resources can include, among other measurable information, memory usage and/or availability (GB), CPU speed (MHz), and start and end hour such as the time when the resource is available or running.

In the embodiment of FIG. 7, for purposes of illustration and not limitation, the collected data can be processed by at least a processing component, such as processing server 7600 of the system 7000, configured with logic to collect, store, and map/or the data to the heatmap representation. In certain embodiments, the processing server 7600 can include a server computer, a desktop computer, a laptop computer, a cloud-based computing device, among other available computing devices. The processing server can comprise one or more processors contained within the one or more other servers, or alternatively, and as depicted in dashed lines in the embodiment of FIG. 7, can be a standalone component configured, for example, to receive and transmit information from and to another server, such as central server 7100.

Based on the collected data related to the one or more teeth, system 7000 can map the data to a heatmap representation of the one or more teeth of the pet. The heatmap representation can use, for example and not limitation, one or more colors, hues, or shadings, to map the data of the one or more teeth. If the data is collected and/or monitored over a given period of time, the duration of time or time intervals at which the data was collected can overlay the visual indicators on the heatmap, as depicted in the embodiment of FIGS. 5A and 5B. The heatmap, or other graphical representation, of the herein disclosed subject matter can be displayed on a graphical user interface at a terminal device 7500, also referred to as a computing device. Terminal device 7500 can include a PC, workstation, user equipment, and/or a mobile device. Accordingly, in some embodiments, the heatmap can be configured to allow users to manipulate or change the heatmap representation displayed on the user interface as through the use of, for example, drop-down menus, radio buttons, or other graphical control elements to selectively display a desired metric on the heatmap, as shown in FIG. 4. In yet another non-limiting embodiment, users can selectively display certain parts of the data, represented on the heatmap by a certain color or visual indicator. In still another non-limiting embodiment, the heatmap representation can be manipulated to display the time-series metric values and/or visual indicators in order from high to low or low to high. Additionally, or alternatively, the heatmap representation can be manipulated to display the data on a drawing or a map of a pet jaw that includes one or more teeth.

By way of example and not limitation, in one embodiment, data related to the one or more teeth of a pet can be collected from the distributed resources 7210-7230, 7310-7330, 7410-7430, by one or more individual servers 7200, 7300, 7400, can be collected and stored in files on the individual servers 7200, 7300, 7400. The files can be any of a plurality of file types such as flat files, database files, markup language files, or the like. The central server 7100 of the embodiment herein described can receive two or more batch file transfers of the collected data from the individual servers 7200, 7300, 7400, respectively. Accordingly, the individual servers 7200, 7300, 7400 can be specifically configured with memory components and file transfer technology to manage and transmit the data to the central server over a network (not shown).

Figure 8:
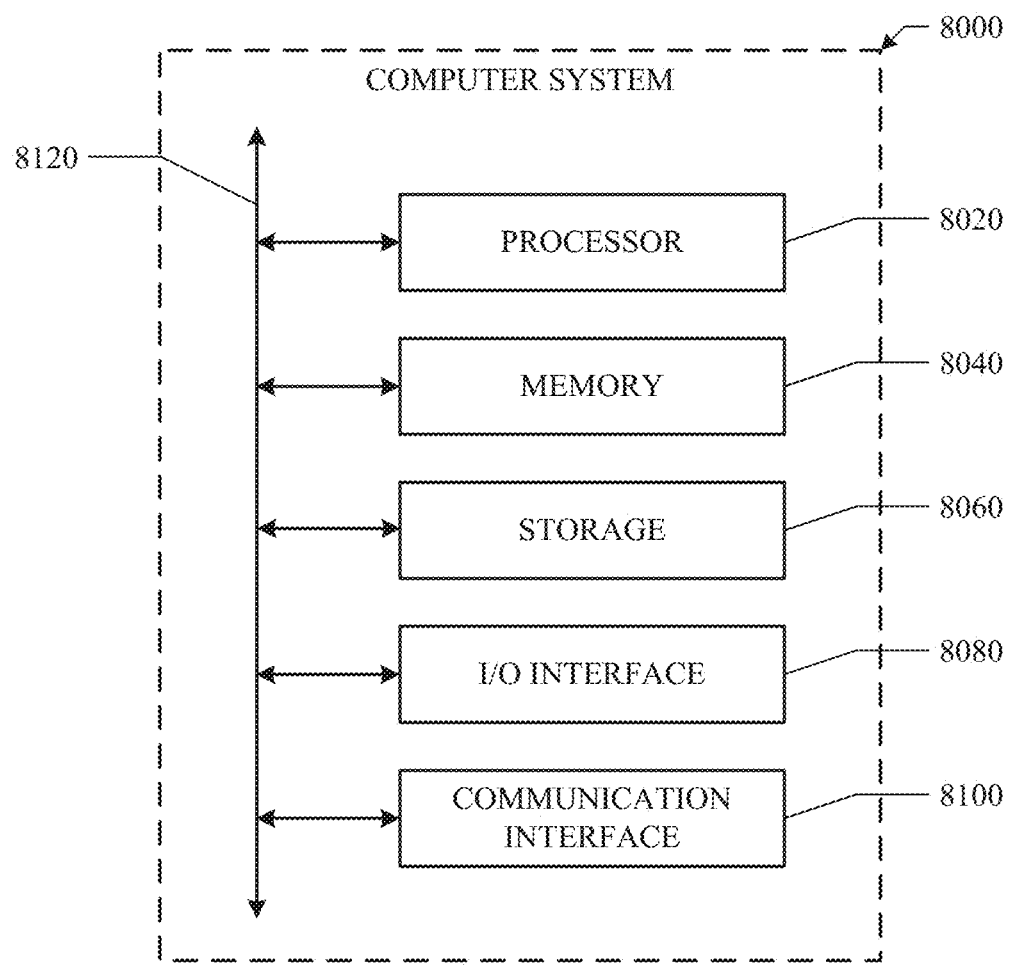
FIG. 8 illustrates a diagram of a system according to certain non-limiting embodiments.

FIG. 8 illustrates a diagram of a system 8000 according to certain non-limiting embodiments. In particular embodiments, one or more computer systems 8000 perform one or more steps of the pet product testing method described or illustrated herein, such as those steps shown in FIG. 6. In some embodiments, one or more computer systems 8000 provide functionality of the server and/or the computing device described or illustrated herein. In certain embodiments, software running on one or more computer systems 8000 performs one or more steps of one or more methods described or illustrated herein or provides functionality described or illustrated herein. Particular embodiments include one or more portions of one or more computer systems 8000. Herein, reference to a computer system can encompass a computing device, and vice versa, where appropriate. Moreover, reference to a computer system can encompass one or more computer systems, where appropriate.

This disclosure contemplates any suitable number of computer systems 8000. This disclosure contemplates computer system 8000 taking any suitable physical form. As example and not by way of limitation, computer system 8000 can be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 8000 can include one or more computer systems 8000; be unitary or distributed; span multiple locations; span multiple machines; span multiple data centers; or reside in a cloud, which can include one or more cloud components in one or more networks. Where appropriate, one or more computer systems 8000 can perform without substantial spatial or temporal limitation one or more steps of one or more methods described or illustrated herein. As an example, and not by way of limitation, one or more computer systems 8000 can perform in real time or in batch mode one or more steps of one or more methods described or illustrated herein. One or more computer systems 8000 can perform at different times or at different locations one or more steps of one or more methods described or illustrated herein, where appropriate.

In particular embodiments, computer system 8000 includes a processor 8020, memory 8040, storage 8060, an input/output (I/O) interface 8080, a communication interface 8100, and a bus 8120. Although this disclosure describes and illustrates a particular computer system having a particular number of particular components in a particular arrangement, this disclosure contemplates any suitable computer system having any suitable number of any suitable components in any suitable arrangement.

In particular embodiments, processor 8020 includes hardware for executing instructions, such as those making up a computer program. As an example, and not by way of limitation, to execute instructions, processor 8020 can retrieve (or fetch) the instructions from an internal register, an internal cache, memory 8040, or storage 8060; decode and execute them; and then write one or more results to an internal register, an internal cache, memory 8040, or storage 8060. In particular embodiments, processor 8020 can include one or more internal caches for data, instructions, or addresses. This disclosure contemplates processor 8020 including any suitable number of any suitable internal caches, where appropriate. As an example and not by way of limitation, processor 8020 can include one or more instruction caches, one or more data caches, and one or more translation lookaside buffers (TLBs). Instructions in the instruction caches can be copies of instructions in memory 8040 or storage 8060, and the instruction caches can speed up retrieval of those instructions by processor 8020. Data in the data caches can be copies of data in memory 8040 or storage 8060 for instructions executing at processor 8020 to operate on; the results of previous instructions executed at processor 8020 for access by subsequent instructions executing at processor 8020 or for writing to memory 8040 or storage 8060; or other suitable data. The data caches can speed up read or write operations by processor 8020. The TLBs can speed up virtual-address translation for processor 8020. In particular embodiments, processor 8020 can include one or more internal registers for data, instructions, or addresses. This disclosure contemplates processor 8020 including any suitable number of any suitable internal registers, where appropriate. Where appropriate, processor 8020 can include one or more arithmetic logic units (ALUs); be a multi-core processor; or include one or more processors 8020. Although this disclosure describes and illustrates a particular processor, this disclosure contemplates any suitable processor.

In particular embodiments, memory 8040 includes main memory for storing instructions for processor 8020 to execute or data for processor 8020 to operate on. As an example and not by way of limitation, computer system 8000 can load instructions from storage 8060 or another source (such as, for example, another computer system 8000) to memory 8040. Processor 8020 can then load the instructions from memory 8040 to an internal register or internal cache. To execute the instructions, processor 8020 can retrieve the instructions from the internal register or internal cache and decode them. During or after execution of the instructions, processor 8020 can write one or more results (which can be intermediate or final results) to the internal register or internal cache. Processor 8020 can then write one or more of those results to memory 8040. In particular embodiments, processor 8020 executes only instructions in one or more internal registers or internal caches or in memory 8040 (as opposed to storage 8060 or elsewhere) and operates only on data in one or more internal registers or internal caches or in memory 8040 (as opposed to storage 8060 or elsewhere). One or more memory buses (which can each include an address bus and a data bus) can couple processor 8020 to memory 8040. Bus 814 can include one or more memory buses, as described below. In particular embodiments, one or more memory management units (MMUs) reside between processor 8020 and memory 8040 and facilitate accesses to memory 404 requested by processor 8020. In particular embodiments, memory 8040 includes random access memory (RAM). This RAM can be volatile memory, where appropriate. Where appropriate, this RAM can be dynamic RAM (DRAM) or static RAM (SRAM). Moreover, where appropriate, this RAM can be single-ported or multi-ported RAM. This disclosure contemplates any suitable RAM. Memory 8040 can include one or more memories 8040, where appropriate. Although this disclosure describes and illustrates particular memory, this disclosure contemplates any suitable memory.

In particular embodiments, storage 8060 includes mass storage for data or instructions. As an example, and not by way of limitation, storage 8060 can include a hard disk drive (HDD), a floppy disk drive, flash memory, an optical disc, a magneto-optical disc, magnetic tape, or a Universal Serial Bus (USB) drive or a combination of two or more of these. Storage 8060 can include removable or non-removable (or fixed) media, where appropriate. Storage 8060 can be internal or external to computer system 8000, where appropriate. In particular embodiments, storage 8060 is non-volatile, solid-state memory. In particular embodiments, storage 8060 includes read-only memory (ROM). Where appropriate, this ROM can be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 8060 taking any suitable physical form. Storage 8060 can include one or more storage control units facilitating communication between processor 8020 and storage 8060, where appropriate. Where appropriate, storage 8060 can include one or more storages 8060. Although this disclosure describes and illustrates particular storage, this disclosure contemplates any suitable storage.

In particular embodiments, I/O interface 8080 includes hardware, software, or both, providing one or more interfaces for communication between computer system 8000 and one or more I/O devices. Computer system 8000 can include one or more of these I/O devices, where appropriate. One or more of these I/O devices can enable communication between a person and computer system 8000. As an example and not by way of limitation, an I/O device can include a keyboard, keypad, microphone, monitor, mouse, printer, scanner, speaker, still camera, stylus, tablet, touch screen, trackball, video camera, another suitable I/O device or a combination of two or more of these. An I/O device can include one or more sensors. This disclosure contemplates any suitable I/O devices and any suitable I/O interfaces 8080 for them. Where appropriate, I/O interface 8080 can include one or more device or software drivers enabling processor 8020 to drive one or more of these I/O devices. I/O interface 8080 can include one or more I/O interfaces 8080, where appropriate. Although this disclosure describes and illustrates a particular I/O interface, this disclosure contemplates any suitable I/O interface.

In particular embodiments, communication interface 8100 includes hardware, software, or both providing one or more interfaces for communication (such as, for example, packet-based communication) between computer system 8000 and one or more other computer systems 8000 or one or more networks. As an example and not by way of limitation, communication interface 8100 can include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 8100 for it. As an example and not by way of limitation, computer system 8000 can communicate with an ad hoc network, a personal area network (PAN), a local area network (LAN), a wide area network (WAN), a metropolitan area network (MAN), or one or more portions of the Internet or a combination of two or more of these. One or more portions of one or more of these networks can be wired or wireless. As an example, computer system 8000 can communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 8000 can include any suitable communication interface 8100 for any of these networks, where appropriate. Communication interface 8100 can include one or more communication interfaces 8100, where appropriate. Although this disclosure describes and illustrates a particular communication interface, this disclosure contemplates any suitable communication interface. Communication interface can be used to receive and/or transmit related to one or more teeth of a pet.

In particular embodiments, bus 8120 includes hardware, software, or both coupling components of computer system 8000 to each other. As an example and not by way of limitation, bus 8120 can include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 8120 can include one or more buses 8120, where appropriate. Although this disclosure describes and illustrates a particular bus, this disclosure contemplates any suitable bus or interconnect.

Herein, a computer-readable non-transitory storage medium or media can include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium can be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments can include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments can provide none, some, or all of these advantages.

What is claimed is:

1. A method for pet product testing comprising:
    collecting, at a server, data related to one or more teeth of a pet obtained via one or more sensors, wherein the data results from the testing of the pet product to the one or more teeth of the pet;
    determining, by the server, a subset of the one or more teeth based on the testing of the pet product;
    receiving, by the server, additional pet data from a user of a terminal device, wherein the additional pet data includes a pet type and/or one or more display options;
    based on the additional pet data, creating, by the server, one or more tooth labels;
    receiving, by the server, tooth identification data from one or more data stores, the tooth identification data including a tooth location assigned to the one or more teeth and a shape identification corresponding to the one or more teeth;
    analyzing, by at least one processor of the server, the tooth identification data and the one or more tooth labels;
    based on the analyzing, transforming, by the server, the data obtained via the one or more sensors to a heatmap representation of the subset of the one or more teeth of the pet based on the tooth identification data and the one or more tooth labels, wherein the heatmap representation illustrates a multi-dimensional graphical representation of the data;
    determining, based on statistical analysis of the data illustrated in the heatmap representation, at least one change to at least one physical characteristic of the subset of the one or more teeth caused by the pet product;
    coloring, by the server, the heatmap representation with at least one color based on the statistical analysis of the data for the subset of the one or more teeth of the pet, wherein the at least one color represents the at least one change to the at least one physical characteristic of the subset of the one or more teeth; and
    displaying, by the server, the heatmap representation with the at least one color indicating the at least one change to the at least one physical characteristic of the subset of the one or more teeth on a user interface of a terminal device.

2. The method for pet product testing according to claim 1, further comprising:
    collecting, at the server, additional data related to the one or more teeth of the pet, wherein the additional data results from the testing of another pet product;
    transforming, by the server, the additional data to another heatmap representation of the one or more teeth of the pet, wherein the another heatmap representation illustrates a graphical representation of the data;
    comparing the heatmap representation of the one or more teeth of the pet related to the pet product and the another heatmap representation of the one or more teeth of the pet related to the another pet product; and
    choosing the pet product or the another pet product based on the comparing of the heatmap representation and the another heatmap representation.

3. The method for pet product testing according to claim 1, wherein the determining of the at least one change to the at least one physical characteristic of the subset of the one or more teeth of the pet is based on the displayed heatmap representation.

4. The method for pet product testing according to claim 3, further comprising:
    providing a user with one or more display options for the heatmap representation at the user interface of the terminal device; and
    changing, at the server, the heatmap representation based on the one or more display options selected by the user.

5. The method for pet product testing according to claim 1, wherein the transforming comprises transforming the data related to the subset of the one or more teeth of the pet to the heatmap using a tooth location.

6. The method for pet product testing according to claim 5, wherein the tooth identification is based on at least one of a type of the pet product testing or a location at which the pet product testing occurs.

7. The method for pet product testing according to claim 1, wherein the coloring of the heatmap representation is based on a breed or breed size of the pet used for the pet product testing.

8. The method for pet product testing according to claim 1, wherein the data comprises at least one of percentage of plaque or calculus on the subset of the one or more teeth or prevalence of periodontal disease for the subset of the one or more teeth of the pet.

9. The method for pet product testing according to claim 1, further comprising:
   starting, at the server, a timer for a duration of time;
   monitoring, at the server, changes to the data related to the subset of the one or more teeth over the duration of the timer; and
   transforming the changes onto the heatmap representation of the subset of the one or more teeth.

10. An apparatus for processing data of a tested pet product comprising:
   at least one processor;
   at least one memory comprising computer program code; and
   wherein the computer program code is configured, when executed by the at least one processor, to cause the apparatus to:
      collect, at the apparatus, data related to one or more teeth of a pet obtained via one or more sensors, wherein the data results from the testing of the pet product to the one or more teeth of the pet;
      determine, by the apparatus, a subset of the one or more teeth based on the testing of the pet product;
      receive, by the apparatus, additional pet data from a user of a terminal device, wherein the additional pet data includes a pet type and/or one or more display options;
      based on the additional pet data, create, by the apparatus, one or more tooth labels;
      receive, by the apparatus, tooth identification data from one or more data stores, the tooth identification data including a tooth location assigned to the one or more teeth and a shape identification corresponding to the one or more teeth;
      analyze, by at least one processor of the apparatus, the tooth identification data and the one or more tooth labels;
      based on the analyzing, transform, by the apparatus, the data obtained via the one or more sensors to a heatmap representation of the subset of the one or more teeth of the pet based on the tooth identification data and the one or more tooth labels, wherein the heatmap representation illustrates a multi-dimensional graphical representation of the data;
      determine, based on statistical analysis of the data illustrated in the heatmap representation, at least one change to at least one physical characteristic of the subset of the one or more teeth caused by the pet product;
      color, by the apparatus, the heatmap representation with at least one color based on the statistical analysis of the data for the subset of the one or more teeth of the pet, wherein the at least one color represents the at least one change to the at least one physical characteristic of the subset of the one or more teeth; and
      display, by the apparatus, the heatmap representation with the at least one color indicating the at least one change to the at least one physical characteristic of the subset of the one or more teeth on a user interface of a terminal device.

11. The apparatus for processing data of a tested pet product according to claim 10, wherein the computer program code is configured, when executed by the at least one processor, to cause the apparatus to:
   collect, at the apparatus, additional data related to the one or more teeth of the pet, wherein the data results from the testing of another pet product;
   transform, at the apparatus, the additional data to another heatmap representation of the one or more teeth of the pet, wherein the another heatmap representation illustrates a graphical representation of the data;
   compare the heatmap representation of the one or more teeth of the pet related to the pet product and the another heatmap representation of the one or more teeth of the pet related to the another pet product; and
   choose the pet product or the another pet product based on the comparing of the heatmap representation and the another heatmap representation.

12. The apparatus for processing data of a tested pet product according to claim 10, wherein the heatmap representation is displayed on a user interface of the terminal device, and the determining of the at least one change to the at least one physical characteristic of the subset of the one or more teeth of the pet is based on the displayed heatmap representation.

13. The apparatus for processing data of a tested pet product according to claim 12, wherein the computer program code is configured, when executed by the at least one processor, to cause the apparatus to:
   receive from a user a selection of one or more display options for the heatmap representation at the user interface of the terminal device; and
   change, at the apparatus, the heatmap representation based on the one or more display options selected by the user.

14. The apparatus for processing data of a tested pet product according to claim 10, wherein the coloring of the heatmap representation is based on a breed or breed size of the pet used for the pet product testing.

15. The apparatus for processing data of a tested pet product according to claim 10, wherein the data comprises at least one of percentage of plaque or calculus on the subset of the one or more teeth or prevalence of periodontal disease for the subset of the one or more teeth.

16. The apparatus for processing data of a tested pet product according to claim 10, wherein the computer program code is configured, when executed by the at least one processor, to cause the apparatus to:
   start, at the apparatus, a timer for a duration of time;
   monitor, at the apparatus, changes to the data related to the subset of the one or more teeth over the duration of the timer; and
   transform the changes onto the heatmap representation of the subset of the one or more teeth.

* * * * *